United States Patent [19]

Swinton

[11] 4,188,948
[45] Feb. 19, 1980

[54] FILTER DEVICE

[75] Inventor: John A. Swinton, Anaheim, Calif.

[73] Assignee: American Hospital Supply Corporation, Evanston, Ill.

[21] Appl. No.: 844,020

[22] Filed: Oct. 20, 1977

[51] Int. Cl.² ............................................. A61M 5/00
[52] U.S. Cl. .................. 128/214 R; 55/159; 128/214 C; 210/436; 210/DIG. 23
[58] Field of Search .......... 128/214 R, 214 C, 214 Z; 210/DIG. 23, 436; 55/158, 159

[56] References Cited
U.S. PATENT DOCUMENTS

| | | | |
|---|---|---|---|
| 3,778,973 | 12/1973 | Martinez | 55/199 |
| 3,905,905 | 9/1975 | O'Leary et al. | 55/159 X |
| 4,009,715 | 3/1977 | Forberg et al. | 128/214 R |
| 4,063,555 | 12/1977 | Ulinder | 128/214 R |

*Primary Examiner*—Dalton L. Truluck
*Attorney, Agent, or Firm*—Edward A. Figg

[57] ABSTRACT

A filter device for connecting in series with a parenteral liquid administration line delivering a medical liquid to a patient. The filter unit includes a housing with a filter member that is previous to liquid but impervious to gas, and a gas collection chamber. A nonpuncturable hypodermic needle guide structure on the unit aligns a hypodermic needle with the gas collection chamber and limits cocking of the needle to prevent puncture or damage to the filter member.

7 Claims, 3 Drawing Figures

FILTER DEVICE

BACKGROUND OF THE INVENTION

Parenteral liquids such as normal saline, 5% dextrose, etc. are frequently administered to a patient from a bottle hanging above the patient which is connected to a flexible tube having at its lower end a needle penetrating the patient's vein. This is frequently referred to as intravenous (I.V.) administration or feeding.

During this administration it is important not to inject any air into the patient's vein as this could cause a serious embolism. One proposal for eliminating any air bubbles or other entrapped air from the administered liquid is described in the Riely U.S. Pat. No. 3,631,654 in which a Y type connector has two dissimilar filters, one passing air, but not liquid, to the atmosphere through one branch; and the other filter passing liquid, but not air, to the patient delivery line. Such type filters sometimes encounter problems with large head pressures created by the hanging bottle causing the air venting filter to seep liquid to the atmosphere.

To provide a more positive control over extraction of the gas, it has been proposed by others, O'Leary et al U.S. Pat. No. 3,905,905 to use a single filter which passes liquid, but not gas, to separate out the gas into a gas collection chamber. Such filter would also filter out any particulate matter that may be in the administration liquid. Rather than automatically venting the collected air or gas to the atmosphere, O'Leary et al periodically extracts it with a hypodermic syringe that pierces a puncturable diaphragm into the gas collecting chamber. In the O'Leary et al device the extraction needle is inserted in very close relationship to the filter membrane so substantially all of the air or gas collected directly above the membrane can be extracted through the syringe needle. Great care must be taken to prevent cocking of the extraction needle and thereby gouging and damaging the filter membrane which could allow both gas and particulate matter to flow through the filter membrane.

SUMMARY OF THE INVENTION

The present invention prevents any damage to the filter membrane and very closely controls the angle of entry of the extraction syringe needle. This invention has a housing with a gas collection chamber and an extraction port on this chamber that includes a substantially nonpuncturable tubular guide for the extraction needle that prevents any contact between the extraction needle and the filter membrane. There is also a nonpuncturable abutting wall surface spaced from the filter membrane that limits the depth of penetration of the extraction needle.

DETAILED DESCRIPTION

Figure 1:
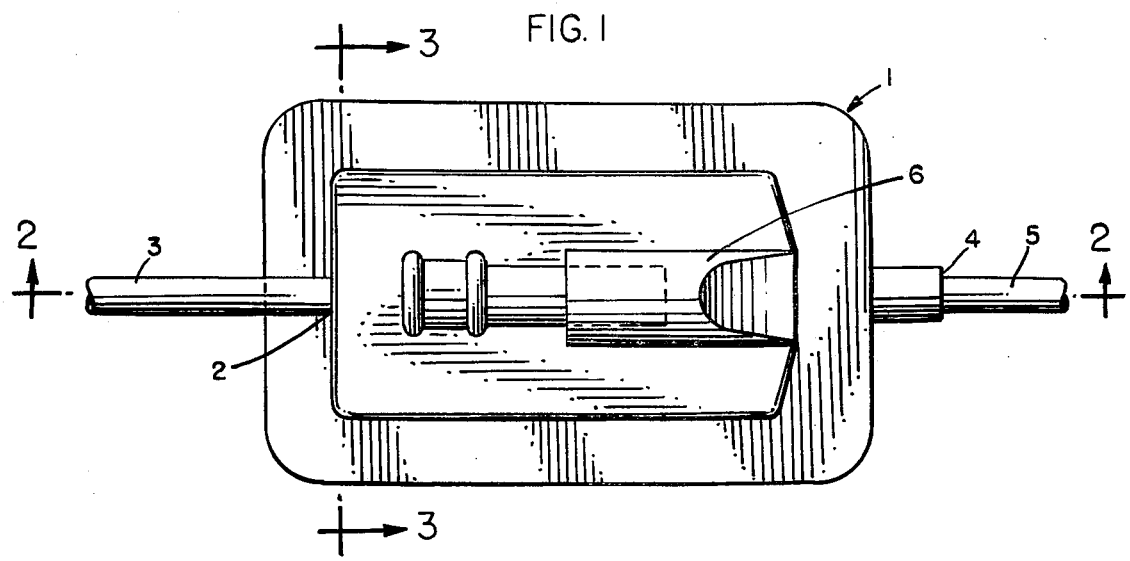
FIG. 1 is a top plan view of the filter unit shown connected in series with the parenteral liquid administration line.

In FIG. 1 the filter unit includes a housing shown generally as 1 with an inlet 2 connected to an upstream portion 3 of a parenteral liquid administration line leading from the parenteral liquid bottle (not shown). An outlet 4 of the housing connects to a portion 5 of the administration line leading to a patient (not shown). A gas collection portion 6 of the housing includes therein a gas collecting chamber 7. A port 8 into chamber 7 has a tubular nonpierceable structure that joins to a tubular nonpierceable adapter 9. At an outer end of adapter 9 is a pierceable resealable rubber diaphragm 10. Adapter 9 and a tubular substantially nonpierceable section 10 of the housing combine to define a tubular guide for a hypodermic needle 11 with a hub 12 and a cannula 13. This needle 11 is attached to a conventional hypodermic syringe 14. A substantially nonpuncturable forward wall 15 of the housing limits the penetration depth of cannula 13.

The housing 1 is separated into an upper chamber containing an unfiltered liquid 16 and a lower chamber containing a filtered liquid 17. This chamber separation is caused by a transverse filter member 18 that is previous to liquid but impervious to gas once wetted and at normal I.V. systems pressures. Preferably a series of supporting ribs such as 19 or 20, support membrane 18 and prevent its inadvertent rupture.

Figure 2:
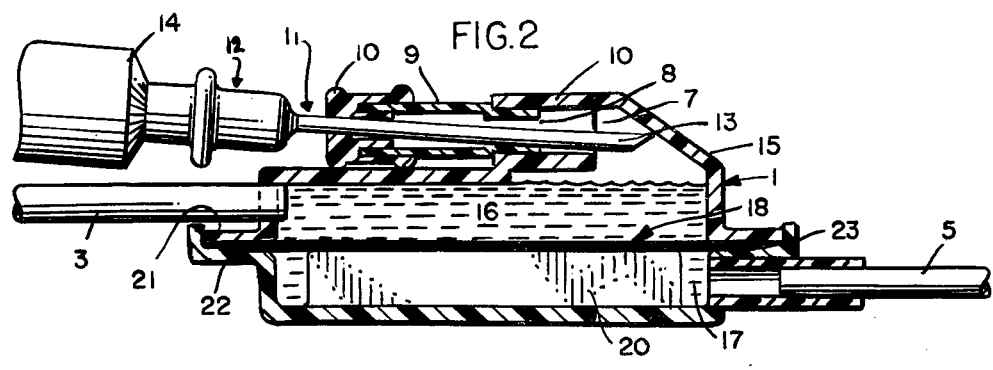
FIG. 2 is a sectional view taken along line 2—2 of FIG. 1.
Figure 3:
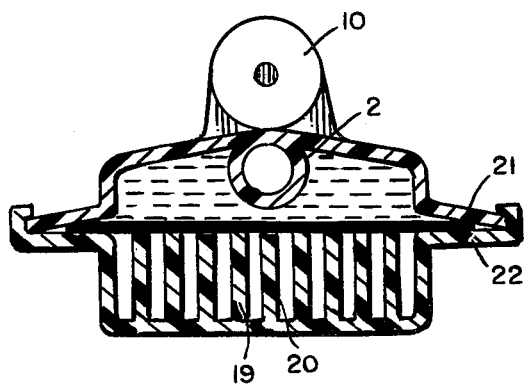
FIG. 3 is a sectional view taken along line 3—3 of FIG. 1.

As shown in FIG. 2, gas collecting chamber has collected a volume of gas which will not pass through membrane 18. Hypodermic needle 11 has been inserted through the tubular substantially nonpuncturable guide structure form by adapter 9 and tubular section 10. The cannula 13 has been cocked to the fullest extreme in FIG. 2 and is still a safe distance from delicate membrane 18. Its depth of penetration is controlled by wall 15. The accumulated gas in gas collecting chamber 7 can be extracted into syringe 14 and needle 11 then removed. Rubber diaphragm 10 then reseals and prevents any liquid seepage from unfiltered liquid in the upper chamber of the housing.

In FIG. 2 the adapter 9 and tubular section 10 are shown in a two-piece construction that is either wedge fitted together or bonded together. It is understood that adapter 9 could be integrally molded with tubular section 10. The important thing is to provide a nonpuncturable guide channel of sufficient length and cross-sectional area relationship to prevent contact between cannula 13 and membrane 18. In FIG. 2 the length of the tubular guide channel is substantially greater than its cross-sectional dimension.

To provide a very firm sealing connection between filter membrane 18 and the housing, the housing is made in separate upper and lower portions which have respectively wide outwardly extending flanges 21 and 22 about their perimeters. These flanges tightly grip and seal the filter membrane 18 therebetween over a wide lateral area. A snap-in or heated sealed edge section 23 on one flange reliably blocks the two flanges together and forms the housing.

In the foregoing description, a specific example has been used to describe the invention. However, it is understood by those skilled in the art that certain modifications can be made to this example without departing from the spirit and scope of the invention.

I claim:

1. A filter device for separating gas from a medical fluid or the like in which a housing has a filter element and a gas collection chamber, wherein the improvement comprises a tubular sleeve guide means in parallel relationship with the filter element, having a passage which is substantially longer than its cross-sectional dimension and which extends substantially the length of the housing, in communication with the gas collection chamber and having an extraction supporting a puncturable diaphragm at the end of said tubular sleeve opposite the gas collection chamber, said tubular sleeve providing means for aligning a gas extraction tool with the interior of the gas collection chamber while simultaneously preventing any contact between the extraction tool and the filter member.

2. The filter device as set forth in claim 1, wherein the housing is segregated by a filter element into a first unfiltered liquid chamber with an inlet port, and a second filtered liquid chamber having a liquid outlet port; and the gas collection chamber has a nonpuncturable abutment wall spaced from the filter member to limit the penetration depth of a gas extraction tool.

3. The filter device as set forth in claim 1, wherein the guide means includes the combined passages of a tubular adapter supporting a puncturable diaphragm at one end, and a tubular section on the housing which couples with the adapter.

4. The filter device as set forth in claim 1, wherein the device is connected in series with a parenteral liquid administration set; and there is in combination with the device a hypodermic syringe needle penetrating the extraction port, and said guide means prevents any cocking of the hypodermic needle to place it in close proximity with the filter member.

5. The filter device as set forth in claim 1, wherein the housing has an inlet port in axial alignment with an inlet tube structure; and the gas extraction port is connected to a tubular guide means that has an axis different from the liquid inlet port.

6. The filter device as set forth in claim 5, wherein the tubular guide means has an axis that is substantially parallel to but spaced from the axis of the inlet port.

7. The filter device as set forth in claim 1, wherein the housing includes an upper member having an external laterally extending flange about its periphery; and a lower member having an external laterally extending flange about its periphery; and the filter member is a membrane that is pervious to liquid but impervious to gas, said filter membrane being sandwiched between these external flanges; and means locking the two flanges together.

* * * * *